United States Patent
Perouse et al.

(10) Patent No.: US 6,565,540 B1
(45) Date of Patent: May 20, 2003

(54) INJECTION SYRINGE WITH NEEDLE SHIELD LOADED WITH A SPRING

(75) Inventors: Eric Perouse, L'Isle Adam (FR); Yves Arnissolle, Saint Genis Laval (FR)

(73) Assignee: Sedat, Irigny (FR)

( * ) Notice: Subject to any disclaimer, the term of this patent is extended or adjusted under 35 U.S.C. 154(b) by 0 days.

(21) Appl. No.: 09/700,667
(22) PCT Filed: May 18, 1999
(86) PCT No.: PCT/FR99/01182
§ 371 (c)(1),
(2), (4) Date: Nov. 17, 2000
(87) PCT Pub. No.: WO99/59658
PCT Pub. Date: Nov. 25, 1999

(30) Foreign Application Priority Data

May 19, 1998 (FR) .............................. 98 06321

(51) Int. Cl.[7] .............................. A61M 5/32
(52) U.S. Cl. ...................... 604/192; 604/198
(58) Field of Search ................ 604/136, 192, 604/198, 110, 208, 263

(56) References Cited

U.S. PATENT DOCUMENTS 4,795,432 A  1/1989  Karczmer .................. 604/110
5,658,259 A * 8/1997 Pearson et al. ............. 604/136

FOREIGN PATENT DOCUMENTS

| FR | 2741268 | 5/1997 |
|----|---------|--------|
| GB | 728248  | 4/1955 |
| WO | 97/14455 | 4/1997 |

* cited by examiner

Primary Examiner—Manuel Mendez
(74) Attorney, Agent, or Firm—Sughrue Mion, PLLC

(57) ABSTRACT

An injection syringe having a body (12) bearing an injection needle (14), a reservoir (16) containing a liquid (42) to be injected and being movable relative to the body (12) for causing the liquid to be injected to circulate through the needle (14), and a needle shield (18) movably mounted relative to the needle (14) for movement, under the control of a spring (20), from a retracted position towards an active protective position. The syringe has complementary parts (54, 62) which, when engaged, retain a first spring (20) end cooperating with the shield (18), and which, when disengaged by further movement of the reservoir (16), release the spring (20) first end to displace the shield (18) to its active protective position. The second spring (20) end is pressed against the reservoir (16) for gradually compressing the spring (20) during injection.

6 Claims, 2 Drawing Sheets

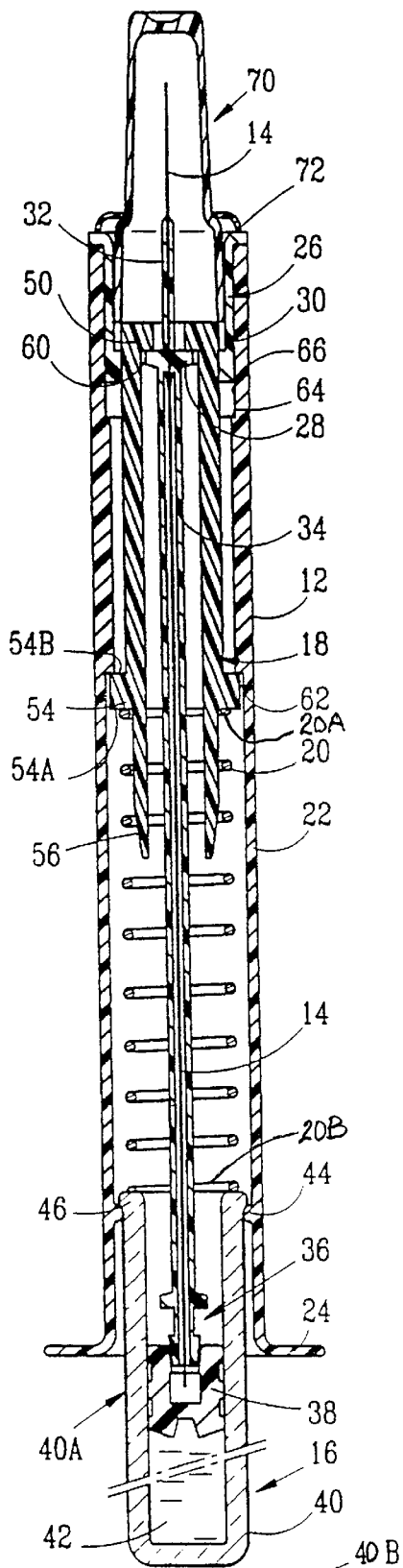
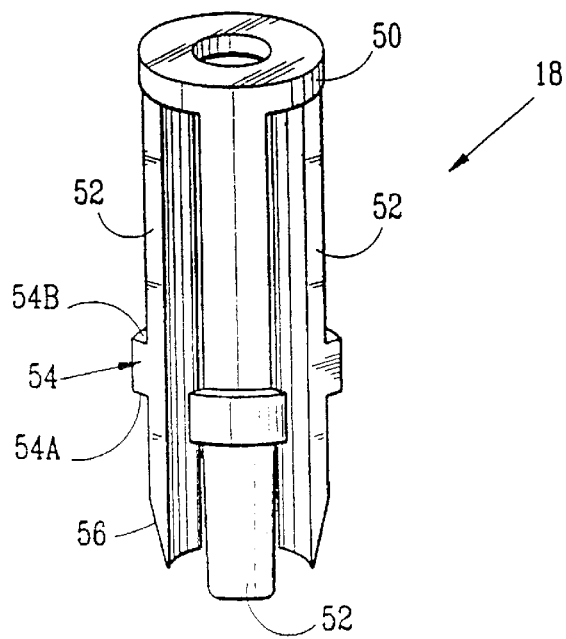
FIG.1
FIG.2

INJECTION SYRINGE WITH NEEDLE SHIELD LOADED WITH A SPRING

BACKGROUND OF THE INVENTION

The present invention relates to an injection syringe of the type comprising a syringe body bearing an injection needle, a reservoir containing a liquid to be injected, which reservoir comprises a moving part mounted so that it can move in sliding with respect to the body so as to cause the liquid to be injected to flow down the injection needle, and a moving needle protector mounted so that it can be moved with respect to the injection needle under the control of a spring, from a retracted position set back from the injection end of the needle to an active protective position in which the front end of the protector is forward of the injection end of the needle, the syringe further comprising means for, during injection, retaining a first end of the spring collaborating with the protector, and means carried by the said moving part for, at the end of injection, releasing the said first end of the spring to cause the protector to move into its active protective position.

Document EP-A-0 467 173, for example, discloses a syringe of the aforementioned type. In a syringe such as this, the needle protector is arranged around the syringe body, of which it constitutes a sheath. The spring that operates the needle protector is initially compressed between the syringe body and the sheath. The sheath is held onto the syringe body by elastic snap-fastening. The syringe piston comprises means for detaching the sheath from the syringe body, which releases the spring and moves the sheath into its active protective position.

As the spring is initially compressed, it has to be compressed during the manufacture of the syringe, which makes it tricky to fit. In addition, as the spring is kept compressed during syringe storage, this spring may experience premature ageing, reducing its performance over time.

SUMMARY OF THE INVENTION

The object of the invention is to provide an injection syringe equipped with a spring-loaded needle protector which does not exhibit the abovementioned drawbacks and which, in particular, is easy to produce and is reliable.

To this end, the subject of the invention is an injection syringe of the aforementioned type, characterized in that the second end of the spring is pressed against the said part of the reservoir that can move with respect to the body to gradually compress the spring during injection.

According to some particular embodiments, the injection syringe has one or more of the following features:

- the said moving part comprises a cylindrical wall closed off by an end forming a reservoir in which there is mounted, so that it can slide, a piston through which the said injection needle passes, the body comprising means for immobilizing the piston at least during injection;
- the injection needle extends over most of the length of the body;
- the said spring is inserted between the said moving part and the protector and the said means for retaining the first end of the spring comprise means for immobilizing the protector with respect to the body, the said means for releasing the first end of the spring comprising means for releasing the protector against which the said first end of the spring rests;
- the protector comprises an end ring extended by legs extending partially up inside the body, the said means for immobilizing the protector comprise complementing projecting and recessed locking profiles borne by the body and the legs, and the said means for releasing the protector comprise means for deforming the legs with a view to disengaging the projecting and recessed complementing profiles; and
- the deforming means comprise, borne by the legs, cam surfaces designed to collaborate with the end of the said moving part.

BRIEF DESCRIPTION OF THE DRAWINGS

The invention will be better understood upon reading the description which will follow and is given merely by way of example and made with reference to the drawings, in which:

FIG. 1 is a view in longitudinal section of a syringe according to the invention in the storage position;

FIG. 2 is a perspective view of the needle protector of the syringe of FIG. 1;

DETAILED DESCRIPTION OF THE INVENTION

Figure 3:
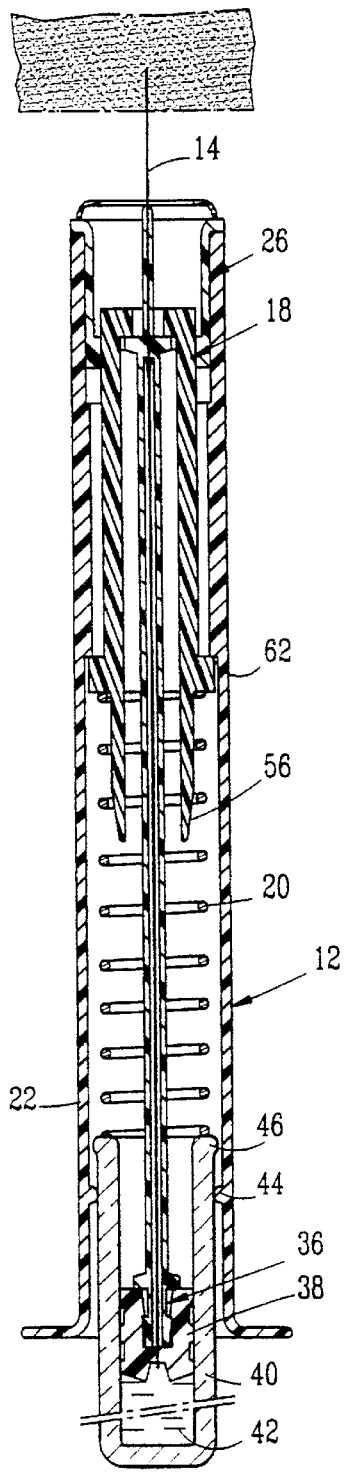
FIG. 3 is a view in longitudinal section of the syringe in the initial phase of injection.

The syringe depicted in FIG. 1 is essentially axisymmetric. It comprises an outer syringe body 12 bearing an injection needle 14, an injection end of which protrudes forward out of the body 12 and the other end of which is intended to be housed inside a reservoir 16 filled with a liquid that is to be injected.

Furthermore, the syringe comprises a needle protector 18 that can be moved between a retracted position and an active protective position under the control of a coil spring 20 inserted between the needle protector 18 and a moving part of the reservoir 16.

The body 12 consists of a cylindrical tube 22 open at both ends. At the rear, it has two lugs 24 on which fingers can press.

A needle holder 26 is push-fitted onto the front end of the body. This needle holder has a transverse wall 28 carrying the needle 14. This transverse wall externally bears a collet 30 for securing against the interior wall of the tube 22. Along the axis of the collet 30, the needle 14 is housed inside an axial block 32 to which it is bonded.

The needle 14 extends along the entire length of the body 12. In its part housed inside the tube 22, the needle 14 is surrounded over most of its length by a sheath 34 formed integrally with the transverse wall 28. The rear end of the needle protrudes axially beyond the sheath 34. The latter at its end has engagement means 36 for a puncturable piston 38 of the reservoir 16.

The reservoir 16 comprises a blind tube 40 forming a moving part thereof. The blind tube 40 comprises a cylindrical lateral wall 40a closed off at one end by an end 40b. The liquid to be injected, denoted 42, is housed in the reservoir thus formed. This reservoir is closed off by the puncturable piston 38. The piston 38 is mounted so that it can slide along the length of the blind tube 40.

The open end of the tube 40 is engaged, as depicted in FIG. 1, in the body 12 at its rear end. Thus, the piston 38 is housed facing the rear end of the needle 14.

On its interior cylindrical surface, the tube 22 has projections 44 designed to collaborate with an external peripheral bulge 46 formed at the open end of the cylindrical wall 40*a*. The projections 44 and the bulge 46 hold the reservoir 16 in the body 12.

The needle protector 18 is depicted on a larger scale in FIG. 2. At its front end it has a rigid ring 50. This ring is axially secured to three elastic legs 52, each defined in a cylindrical surface extending the ring 50.

Each leg 52 externally comprises a peripheral projection 54 defining axially, on each side of it, two transverse fronts 54*a*, 54*b*. The free ends of the outer lateral surfaces of the legs 52 define ramps 56 inclined towards the axis of the protector. Thus, at its end, the protector 18 has an outside diameter that diminishes gradually towards the end. The ramps 56 are frustoconical portions.

As depicted in FIG. 1, most of the lengths of the legs 52 is engaged up inside the body 12 through curved openings 60 formed in the transverse wall 28. Only the end ring 50 is kept outside the body 12 and surrounds the block 32 supporting the needle.

On its interior cylindrical surface, the tube 22 in its central part has a shoulder 62 oriented towards the rear and defining a recessed profile. This is designed to collaborate with the fronts 54*a* defined by the projections 54, so as to retain the protector 18 with respect to the body 12 by elastic snap-fastening.

Similarly, the interior cylindrical surface of the tube 22 comprises, in its front part, a shoulder 64 orientated forward. This shoulder 64 defines, with the collet 30, a peripheral groove 66 on the interior wall of the body. This groove 66 is designed to accommodate the projections 54 of the protector, so as to immobilize it in its active protective position, the fronts 54*b* then collaborating with the shoulder 64.

As shown in FIG. 1, the spring 20 is inserted between the end of the moving part 40 of the reservoir and the needle protector 18. More specifically, a first end of the spring 20*a* presses on the rear fronts 54*b* of the projections 54 and the second end of the spring 20*b* presses on the end of the blind tube 40 along the thickness thereof.

Finally, at its front end, the syringe has a cap 70 for protecting the injection end of the needle 14. This cap is held in place by elastic clips 72 formed integrally with the needle holder 26.

The syringe according to the invention works as follows.

In order to give an injection, the practitioner removes the cap 70 by pulling it axially. Holding the syringe between two fingers pressing against the lugs 24, and pressing his thumb onto the end 40*b* of the reservoir, he drives the moving part 40 thereof into the body 12 until the piston 38 becomes impaled on the rear end of the needle 14, as depicted in FIG. 3.

In this position, the liquid 42 contained in the reservoir can be removed through the needle 14. The injection end of the needle 14 is then stuck into the patient's flesh.

To actually give the injection, the practitioner gradually drives the moving part 40 of the reservoir into the body 12. Thus, with the punctured piston 38 kept immobilized outside the sheath 34, the liquid 42 gradually flows down the needle 14.

Figure 4:
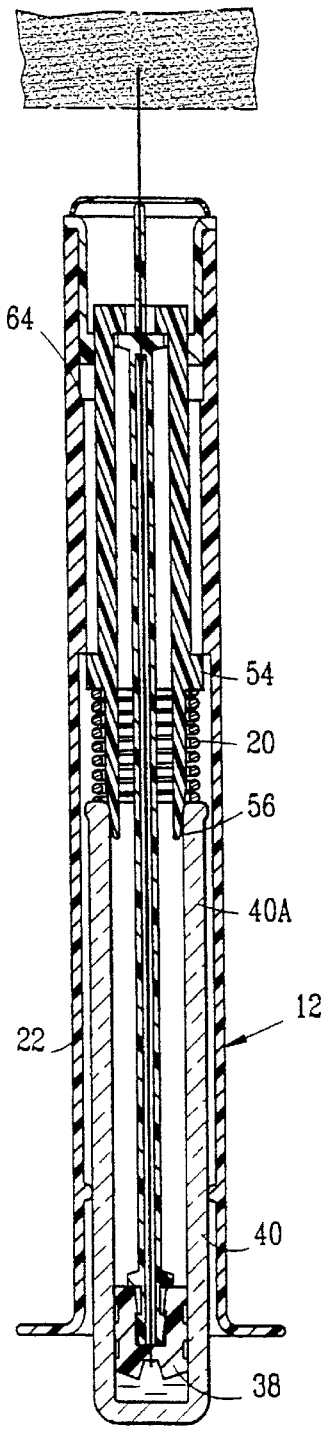
FIG. 4 is a view in longitudinal section of the syringe- .during injection.

At the same time, as the moving part 40 moves in translation, the spring 20 is gradually compressed to a state depicted in FIG. 4 where the spring is practically coil-bound.

In this position, the ramps 56 carried at the ends of the legs 52 are engaged inside the cylindrical wall 40*a* of the moving part of the reservoir. These ramps, which constitute cam surfaces, collaborate with the end of the moving part 40 to cause the legs to deform towards the axis of the syringe. Thus, shortly before the injection is completed, the projections 54 are practically disengaged from the peripheral shoulder 62.

When the practitioner drives the moving part 40 even further into the body 12, the projections 54 which initially retained the needle protector 18 completely come free of the shoulder 62. Thus, the needle protector 18 is thrown forward under the action of the compressed spring 20, the means hitherto retaining it having been released.

Figure 5:
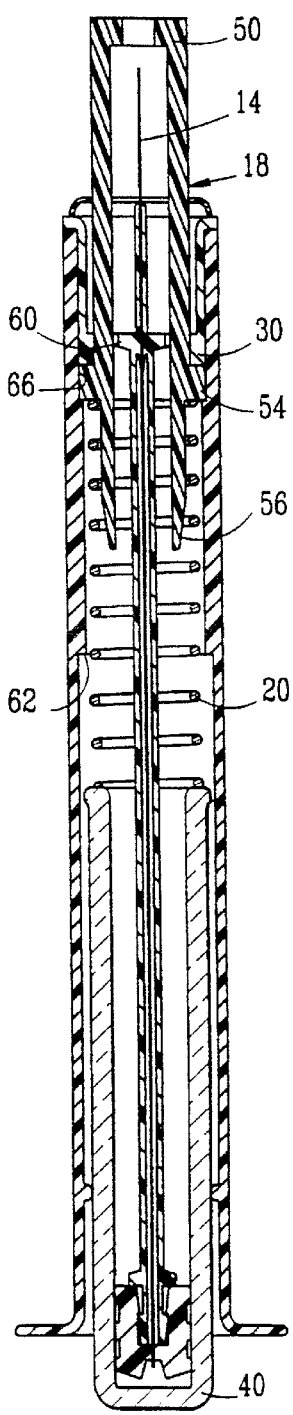
FIG. 5 is a view in longitudinal section of the syringe immediately after the needle protector has automatically been put into place

The needle protector 18 therefore moves, under the action of the spring 20 gradually relaxing, into its closing-off position depicted in FIG. 5. In this position, its end formed by the ring 50 is located beyond the injection end of the needle 14. In this position, the projections 54 are housed elastically in the peripheral groove 66 carried by the body. Thus, the needle protector 18 is held in its active protective position by elastic snap-fastening.

This elastic snap-fastening of the protector prevents any risk of stick injury from the injection end of the needle.

It will be understood that with a syringe such as this, the actuation spring of the needle protector is compressed only for a short period of time, the spring being gradually compressed during injection and immediately released at the end of injection.

During phases in which the syringe is in storage, the spring is compressed only to a small extent and does not need to store up the energy needed to later move the needle protector. Thus, the risks of premature spring ageing and the difficulty of assembling the syringe are avoided.

What is claimed is:

1. An injecting syringe of the type comprising a syringe body (12) bearing an injection needle (14), a reservoir (16) containing a liquid (42) to be injected, which reservoir (16) comprises a moving part (40) mounted so that it can slidably move with respect to the body (12) so as to cause the liquid to be injected to flow down the injection needle (14), and a moving needle protector (18) mounted so that it can be moved, with respect to the injection needle (14), under the control of a spring (20) from a retracted position set back from an injection end of the needle (14) to an active protective position in which a front end of the protector (18) is forward of the injection end of the needle (14), the syringe further comprising means (54, 62) for, during injection, retaining a first end (20*a*) of the spring (20) collaborating with the protector, and means carried by said moving part (40) for, at the end of injection, releasing said first end (20*a*) of the spring (20) to cause the protector (18) to move into its active protective position, characterized in that a second end (20*b*) of the spring (20) is pressed against said moving part of the reservoir (40) to gradually compress the spring (20) during injection.

2. Injection syringe according to claim 1, characterized in that the said moving part (40) comprises a cylindrical wall (40*a*) closed off by an end (40*b*) forming a reservoir in which there is mounted, so that it can slide, a piston (38) through which the said Injection needle (14) passes, the body comprising means (36) for immobilizing the piston at least during injection.

3. Injection syringe according to claim 2, characterized in that the injection needle (14) extends over most of the length of the body (12).

4. Injection syringe according to claim 1, characterized in that the said spring (20) is inserted between the said moving part (40) and the protector (18), and in that the said means for retaining the first end of the spring comprise means (54, 62) for immobilizing the protector (18) with respect to the body (12), the said means for releasing the first end (20a) of the spring (20) comprising means (56) for releasing the protector (18) against which the said first end (20a) of the spring (20) rests.

5. Injection syringe according to claim 4, characterized in that the protector (18) comprises an end ring (50) extended by legs (52) extending partially up inside the body (12), in that the said means for immobilizing the protector (18) comprise complementing projecting and recessed locking profiles (54, 62) borne by the body (12) and the legs (52), and in that the said means for releasing the protector comprise means (56) for deforming the legs (52) with a view to disengaging the projecting and recessed complementing profiles (54, 62).

6. Injection syringe according to claim 5, characterized in that the deforming means comprise, borne by the legs (52), cam surfaces (56) designed to collaborate with the end of the said moving part (40).

\* \* \* \* \*